(12) United States Patent
El-Halwagi et al.

(10) Patent No.: US 8,802,905 B2
(45) Date of Patent: Aug. 12, 2014

(54) INTEGRATED BIOFUEL PROCESSING SYSTEM

(75) Inventors: Mahmoud M. El-Halwagi, College Station, TX (US); Kenneth R. Hall, College Station, TX (US); Harold Dennis Spriggs, Leesburg, VA (US)

(73) Assignees: The Texas A&M University System, College Station, TX (US); Byogy Renewables, Inc., San Jose, CA (US)

( * ) Notice: Subject to any disclaimer, the term of this patent is extended or adjusted under 35 U.S.C. 154(b) by 266 days.

(21) Appl. No.: 13/378,602

(22) PCT Filed: Jun. 18, 2010

(86) PCT No.: PCT/US2010/039246
§ 371 (c)(1),
(2), (4) Date: Dec. 15, 2011

(87) PCT Pub. No.: WO2010/148348
PCT Pub. Date: Dec. 23, 2010

(65) Prior Publication Data
US 2012/0095272 A1     Apr. 19, 2012

Related U.S. Application Data

(60) Provisional application No. 61/218,746, filed on Jun. 19, 2009.

(51) Int. Cl.
*C10L 1/04* (2006.01)
(52) U.S. Cl.
USPC ............... 585/240; 285/7; 285/14; 285/241; 285/242; 285/310; 585/317; 585/318; 585/321; 585/324; 585/469; 585/638; 44/605; 44/606
(58) Field of Classification Search
USPC ............ 585/7, 14, 240–242, 310, 317–318, 585/324, 469, 638, 733; 44/605–606
See application file for complete search history.

(56) References Cited

U.S. PATENT DOCUMENTS

| | | | |
|---|---|---|---|
| 4,621,164 | A | 11/1986 | Chang et al. |
| 5,877,372 | A | 3/1999 | Evans et al. |

(Continued)

FOREIGN PATENT DOCUMENTS

| | | | | |
|---|---|---|---|---|
| WO | WO 2004/108609 A1 | * | 12/2004 | ............... C02F 3/00 |
| WO | WO 2008/067627 A2 | * | 6/2008 | .............. C07C 27/06 |

(Continued)

OTHER PUBLICATIONS

Svejda, S.A. et al. (1999). Organometallics, 18, 65-74.*

(Continued)

*Primary Examiner* — Brian McCaig
(74) *Attorney, Agent, or Firm* — Edwin S. Flores; Chalker Flores, LLP

(57) ABSTRACT

A unique, integrated non-obvious pathway to convert biomass to biofuels using integration of chemical processes is described herein. The present invention is simple, direct, and provides for the shortest or minimum path between biomass and transportation fuels with alcohols as intermediates, while avoiding hydrogen use during processing. Furthermore, the present invention allows the manufacture of "drop-in" substitutable fuels to be used as-is without modifications instead of conventional petroleum based fuels. The processing described herein is done under mild conditions, under relatively low pressures and temperatures, and under non-corrosive conditions obviating use of special equipment or materials. The novel integration heat and mass generated during the process increases overall process efficiency and lowers financial costs for processing and capital equipment, manages environmental impact, and enables a relatively high degree of yield by an enhanced usage of fresh water and thermal energy in comparison to the amount of biomass processed.

16 Claims, 1 Drawing Sheet

(56) References Cited

U.S. PATENT DOCUMENTS

| | | |
|---|---|---|
| 6,620,292 B2 | 9/2003 | Wingerson |
| 2005/0112739 A1 | 5/2005 | Golubkov |
| 2005/0269048 A1 | 12/2005 | Rodriguez et al. |
| 2008/0121359 A1 | 5/2008 | Holtzapple et al. |

FOREIGN PATENT DOCUMENTS

| | | |
|---|---|---|
| WO | 2010039246 A1 | 4/2010 |
| WO | 2010148348 A2 | 12/2010 |

OTHER PUBLICATIONS

Albertazzi, S., et al., "The Technical Feasibility of Biomass Gasification for Hydrogen Production," Catalysis Today, (2005), pp. 297-300.

Costa, Enrique, et al., "Ethanol to Gasoline Process: Effect of Variables, Mechanism, and Kinetics," Ind. Eng. Chem. Process Des. Dev., (1985) 24:239-244.

Golombok, Michael, et al., "Dimerization of n-Butenes for High Octane Gasoline Components," Ind. Eng. Chem. Res., (2000), 39:267-271.

International Search Report and Written Opinion for PCT/US2010/039246, dated Feb. 1, 2011, 9 pages.

Lallemand, Michael, et al., "Catalytic Oligomerization of Ethylene over Ni-Containing Dealuminated Y Zeolites," Applied Catalysis A: General 301, (2006), pp. 196-201.

Lin, Yan, et al., "Ethanol Fermantation from Biomass Resources: Current State and Prospects," Appl. Microbiol. Biothechnol., (2006), 69:627-642.

Ouyang, Jia, et al., "Catalytic Conversion of Bio-Ethanol to Ethylene over La-Modified HZSM-5 Catalysts in a Bioreactor," Catal. Lett., (2009), 132:64-74.

Takahara, Isao, et al., "Dehydration of Ethanol into Ethylene over Solid Acid Catalysts," Catalysis Letters, Dec. 2005, vol. 105, Nos. 3-4, pp. 249-252.

Whitcraft, David R., et al., "Recovery of Ethanol from Fermentation Broths by Catalytic Conversion to Gasoline," Ind. Eng. Chem. Process Des. Dev., (1983), 22:452-457.

Xiao, Yanyan, et al., "Catalytic Dehydration of Ethanol to Ethylene on TiO2/4Z Zeolite Composite Catalysts," Catal. Lett., (2009), 130:308-311.

* cited by examiner

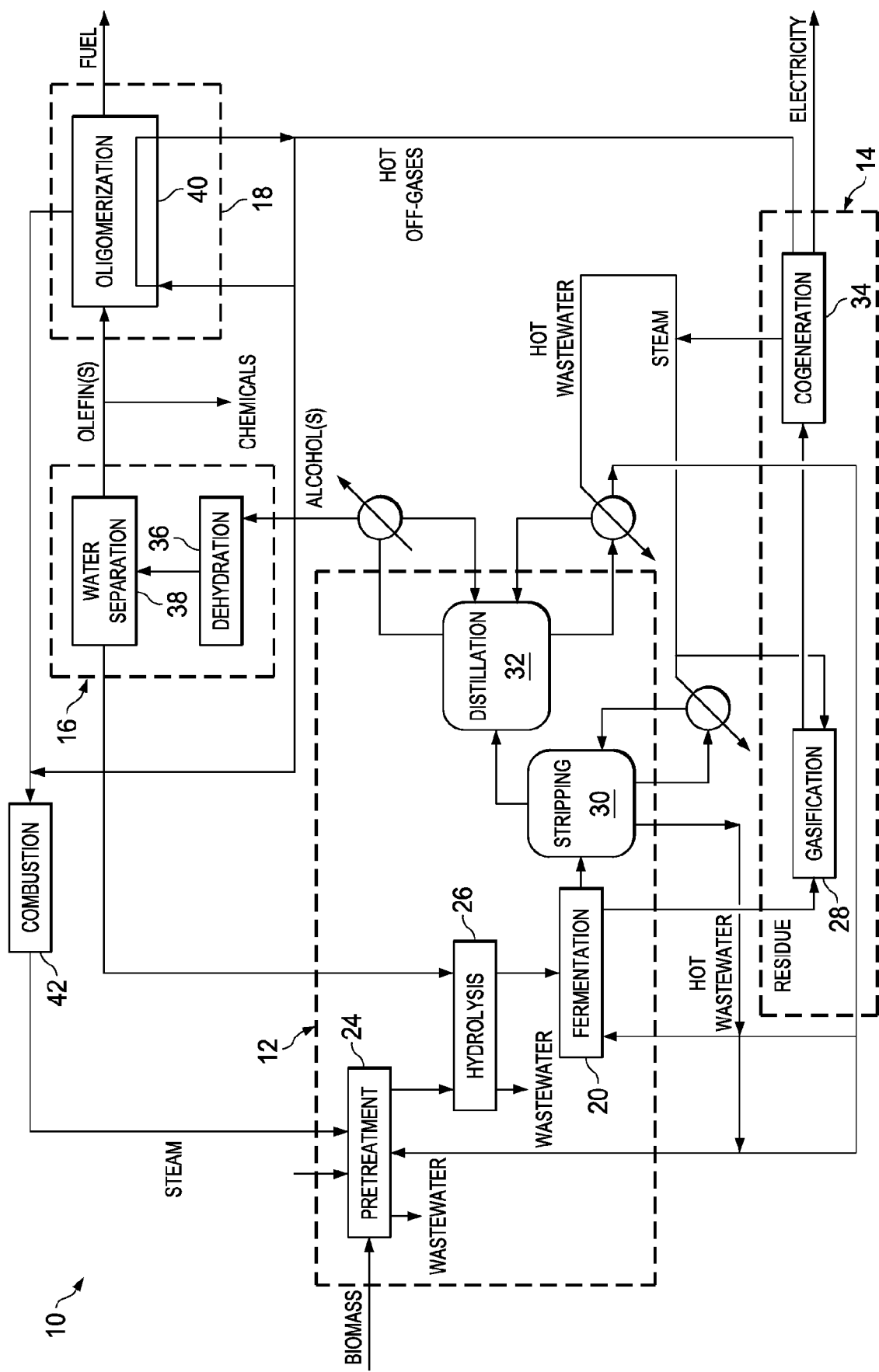

INTEGRATED BIOFUEL PROCESSING SYSTEM

CROSS-REFERENCE TO RELATED APPLICATIONS

This application claims priority to U.S. Provisional Application Ser. No. 61/218,746, filed Jun. 19, 2009, and claims priority to and is a 35 U.S.C. §371, National Phase filing of PCT Application Serial No. PCT/US2010/039246, filed Jun. 18, 2010, the entire contents of both are incorporated herein by reference.

TECHNICAL FIELD OF THE INVENTION

This disclosure generally relates to biofuels, and more particularly, to integrated systems and methods for converting biomass to biofuels.

BACKGROUND ART

Biological matter that has been converted to liquefied fuel is generally referred to as biofuel. Biofuel processes that create these biofuels often use biological processing methods that produce alcohols, such as ethanol. Although these alcohols may have relatively high octane ratings, they have several disadvantages. For example, alcohols have a relatively lower energy density than hydrocarbons, such as gasoline (usually 60-75%). Their relatively strong polarity increases the vapor pressure of fuels when added as a constituent such that air pollution is increased. Alcohols also have a tendency to absorb water. This may be problematic when shipping low-molecular-weight alcohols, such as ethanol, in common-carrier pipelines that may contain water. Ethanol is also corrosive, and thus may damage pipelines or dissolve fiberglass fuel tanks and motor seals. Additionally, because ethanol is miscible with both water and organics, ethanol spills can result in the transport of benzene, toluene, xylene, etc. into the ground water. Finally, it is difficult to extinguish ethanol fires, and fire fighters need additional training and equipment to address this danger. Therefore, it is important to identify cost-effective pathways to convert biomass to liquid transportation fuels such as gasoline, diesel, and jet fuels. It is advantageous to have alcohols as intermediates because of the existing infrastructure for the production of alcohols. It is also useful to have methods that directly convert alcohols to liquid transportation fuels and to develop mass and energy integration schemes that improve the overall efficiency of the process.

DISCLOSURE OF THE INVENTION

The invention discloses methods and systems for the conversion of biomass to liquid fuels, such as those suitable for powering internal combustion engines, e.g., gasoline, jet engines, e.g., Jet-A, diesel fuel, and industrial boilers. The invention also discloses methods and system for creating other valuable chemicals from biomass. The methods and systems described herein benefit from the symbiotic use of mass (chemical species) and energy converted by one subsystem to increase the overall efficiency of the entire system.

In one embodiment, the biofuel processing system of the invention comprises a biomass conversion subsystem, a gasification subsystem, a dehydration subsystem, and a fuel conversion subsystem. The biomass conversion subsystem is for processing biomass and converting it into alcohols. The biomass conversion subsystem uses a biological process to create alcohol(s) from a biomass while producing some amount of residual biomass and gaseous byproducts (e.g., carbon dioxide).

In one embodiment the instant invention provides an integrated biofuel production process comprising the steps of: (a) converting a biomass to yield one or more alcohols and a residual biomass, (b) gasifying the residual biomass to produce carbon monoxide, hydrogen or mixtures thereof, thereby producing thermal energy, (c) synthesizing a liquid hydrocarbon fuel from the alcohols through a dehydration and an oligomerization reaction using at least a portion of the thermal energy produced by gasifying the residual biomass, and converting the residual biomass into energy and/or one or more commercially viable co-products, wherein the co-products are selected from the group consisting of acids, ketones, alcohols, ethers, alkylbenzenes, fuel additives, biopolymers, proteins for animal and human consumption, and surfactants. The biomasses that can be used in the process described hereinabove are selected from the group consisting of grasses, trees, canes, animal waste, food waste, algae, municipal solid waste green waste, purpose grown non-food energy crops, harvest residuals, and other waste and crop biomass materials. In one aspect the process described above further comprises the step of combusting the carbon monoxide, the hydrogen, or mixtures thereof to produce heat and electricity, wherein the heat and electricity are recycled back into the process to perform the step of synthesizing the liquid hydrocarbon fuel. In another aspect of the instant invention at least a portion of the thermal energy produced by the gasification of the residual biomass is recycled back into the process to perform the step (a) described above.

The biomass conversion subsystem may include a pretreatment subsystem, a hydrolysis subsystem and a fermentation subsystem. The pretreatment step typically includes multiple options: (1) initial pretreatment can be the segregation or classification of biomass waste such as MSW into components for further processing and (2) subsequent pretreatment can include fractionating the biomass into its constituent parts, e.g., cellulose, hemi-cellulose and lignin. These can each then be processed independently into fuels, chemicals, energy or useful co-products. In yet another aspect the pretreatment and hydrolysis processes are done by using hot wastewater. The pretreatment subsystem breaks down the cellulose and the hemicellulose structures of biomass to aid in further processing. This pretreatment process may be any known process that works to break down cellulose and hemicellulose materials, such as cavitation methods, micronization methods, chemical treatment methods, grinding methods or any other suitable method. The hydrolysis subsystem then converts the preprocessed cellulose and hemicellulose materials from the pretreatment process into sugars. It is also possible to combine pretreatment with hydrolysis such as the methods of biomass fractionation and hydrolysis (e.g., U.S. Pat. No. 6,620,292 B2/2003 incorporated by reference herein) or acid-catalyzed separation and enzymatic hydrolysis (e.g., US Patent Application Publication No. 20050269048 A1/2005 incorporated by reference herein). The fermentation subsystem may include a fermenter, a stripping column and a distillation column. The fermentation might differ depending on what sugar is generated from the biomass. The sugar can be "free sugars" as found in cane or other C5 and C6 sugars that can be generated from cellulose and hemi-cellulose. The fermenter takes the sugars from the hydrolysis subsystem and produces an alcohol broth (e.g., ethanol and/or higher alcohols and water) and a solid residue (primarily lignin and ash or char). The broth then passes through the stripping column and the distillation column.

Suitably, the distillation column has a partial condenser that allows the top product to leave the distillation column as ethanol vapor. It is also possible to use other methods for concentrating the alcohol (e.g., membrane systems). It is worth noting that the alcohol need not be concentrated to high-purity levels (e.g., no need to exceed azeotropic concentration in the case of ethanol).

The gasification subsystem takes the residual material from the fermenter (e.g., lignin, unreacted cellulose and hemicellulose) and generates syngas (carbon monoxide and hydrogen) producing thermal energy. The thermal energy is captured and used to heat processes in the biomass conversion subsystem and/or the fuel conversion subsystem. The syngas produced from gasification can be used in a cogeneration unit that produces steam, energy as heat (from the hot off-gasses) and electric power. Alternatively, the lignin and hemicellulose may be converted to other valuable co-products. Non-limiting examples of co-products include but are not limited to acids, ketones, alcohols, ethers, alkylbenzenes, fuel additives, biopolymers, proteins for animal and human consumption, and surfactants. The steam from the cogeneration system can be used by the gasifier and by reboiler systems. The heat from the hot-gasses of the cogeneration system can be used by the dehydration and fuel generation subsystems. The hot water produced from the reboilers can be used by the stripping and distillation columns and can also be used for mass and heat integration in the pretreatment system and the hydrolysis system, thereby saving fresh water and heat required in the pretreatment and hydrolysis systems. There may be other heat and power integration options, the system described hereinabove is merely for illustration purposes.

In one aspect the one or more alcohols generated in step (a) of the process are further converted to one or more olefins by a dehydration reaction, wherein the one or more olefins are selected from the group consisting of ethylene, propylene, butene, iso-butylene, and combinations and modifications thereof. A dehydration subsystem may be used to convert the alcohols received from the pretreatment system to olefins and remove water from the vapor. For instance, ethanol is dehydrated to ethylene and water. The produced olefins are available at this point for chemical manufacturing or for feed into the fuel generation subsystem to produce fuel. The conversion of olefins to chemicals is not an essential step but merely an option for enhancing the process. In another aspect the one or more olefins undergo an oligomerization in an oligomerization reactor in step (c) to generate one or more commercially viable products selected from the group consisting of chemicals, transportation fuels, linear and branched higher olefins, feedstock, detergents, petrochemicals, oil additives, and high-octane gasoline. In a specific aspect the alcohol is ethanol, wherein the ethanol is further dehydrated in the process to yield ethylene. In yet another aspect the step (c) further comprises an oligomerization step for converting the olefin (e.g., ethylene) to a hydrocarbon fuel. In another aspect the instant invention describes a hydrocarbon fuel produced by the process described hereinabove.

The fuel conversion system produces a mixture of liquid hydrocarbons (e.g. gasoline) from the alcohols. The fuel conversion system utilizes an oligomerization process to perform the conversion of olefins (such as ethylene) to fuel. Using bifunctional catalysts, it is also possible to feed the alcohols to this unit, and it can dehydrate the alcohol(s) into olefin(s) and subsequently convert the olefin(s) into fuel. The off-gasses of the oligomerization system can be burned to provide steam needed by other systems such as the distillation column, stripping column, gasification system, pretreatment process, fermenter, and/or the dehydration subsystem.

Another embodiment of the present invention relates to a chemical production process comprising the steps of: converting a biomass to one or more alcohols and a residual biomass, gasifying the residual biomass to produce one or more hydrocarbon gasses, carbon monoxide, hydrogen or mixtures thereof; and synthesizing one or more chemicals from the alcohols and the hydrocarbon gases, carbon monoxide, hydrogen, or mixtures thereof. In one aspect the chemicals is selected from the group consisting of paraffins, olefins, aromatics, and naphthas. In another aspect the chemical is selected from the group consisting of ethylene, acetylene, benzene, cyclohexene, xylene, toluene, ethylbenzene.

In yet another embodiment the present invention discloses a process for making one or more hydrocarbon fuels from one or more alcohols comprising the steps of dehydrating the one or more alcohols to yield one or more olefins and oligomerizing the one or more olefins in an oligomerization reactor to yield one or more commercially viable products selected from the group consisting of chemicals, transportation fuels, linear and branched higher olefins, feedstock, detergents, petrochemicals, oil additives, and high-octane gasoline. In one aspect the process described above is a "stand-alone" process or can be implemented as a "bolt-on" addition to existing alcohol producing plants. In a specific aspect the present invention described a hydrocarbon fuel made by the above process.

One embodiment of the instant invention relates to an integrated biofuel production process comprising the steps of: (i) pretreating a biomass, (ii) hydrolyzing the converted biomass, wherein the pretreatment and hydrolysis processes are done by using a hot wastewater, (iii) converting a biomass to yield one or more alcohols and a residual biomass, (iv) gasifying the residual biomass to produce carbon monoxide, hydrogen or mixtures thereof, thereby producing thermal energy, wherein at least a portion of the thermal energy produced by the gasification of the residual biomass is recycled back into the process to perform step (iii), (iv) synthesizing a liquid hydrocarbon fuel from the alcohols using at least a portion of the thermal energy produced by gasifying the residual biomass, and (v) converting the residual biomass into one or more commercially viable co-products, wherein the co-products are selected from the group consisting of acids, ketones, alcohols, ethers, alkylbenzenes, fuel additives, biopolymers, proteins for animal and human consumption, and surfactants.

In one aspect the biofuel production process further comprises the step of combusting the carbon monoxide, the hydrogen, or mixtures thereof to produce heat and electricity, wherein the heat and electricity are recycled back into the process to perform step (iii). In another aspect the biomass is selected from the group consisting of grasses, trees, canes, animal waste, food waste, algae, municipal solid waste green waste, purpose grown non-food energy crops, harvest residuals, and other waste and crop biomass materials. In yet another aspect the one or more alcohols generated in step (i) are further converted to one or more olefins by a dehydration reaction, wherein the one or more olefins are selected from the group consisting of ethylene, propylene, butene, iso-butylene, and combinations and modifications thereof. Finally, the instant invention describes a biofuel produced by the above process.

Other embodiments of the present invention may comprise a combination of different biomass conversion processes, and/or a combination of fuel synthesis processes. Such embodiments may comprise multiple biomass conversion processes, such as anaerobic fermentation and anaerobic digestion, and then combine the residual biomass for a single gasification process.

Some embodiments of the disclosure provide numerous technical advantages. Some embodiments may benefit from some, none, or all of these advantages. For example, according to one embodiment, a fuel may be produced having a relatively high energy density that may be generally compatible with commonly used fuels, such as gasoline or jet fuel. The biomass processing system includes a number of processing steps that may enable conversion of a relatively large portion of the energy content of the biomass ingredient. The efficiency of the conversion process may be enhanced by utilizing heat and/or mass from one process as an ingredient to another process. Thus, the biomass processing system may enable a relatively high degree of yield and a reduced usage of fresh water and thermal energy in relation to the amount of biomass introduced into the biofuel processing system. Other technical advantages may be readily ascertained by one of ordinary skill in the art.

DESCRIPTION OF THE DRAWINGS

A more complete understanding of embodiments of the disclosure will be apparent from the detailed description taken in conjunction with the accompanying drawings in which:

FIG. 1 is a diagram showing a generalized embodiment of a biofuel processing system according to the teachings of the present disclosure.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Before any embodiments of the invention are described in detail, it is to be understood that the invention is not limited in its application to the details of construction and the arrangement of components set forth in the following description. The invention is capable of other embodiments and of being practiced or of being carried out in various ways. Also it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items.

As used herein, the term "hydrocarbon" refers to any molecule consisting of carbon and hydrogen in any combination. As such, "hydrocarbon" includes straight-chain, branched, and cyclic alkanes, alkenes, alkynes, and aromatics.

As used herein, the term "alcohol" and "alcohols" refers to any of a number of carbon/hydrogen-containing molecules having one or more singly-bonded hydroxyl (OH) groups. The term "alcohol" encompasses both primary (e.g. OH on terminal carbon) and secondary (e.g. OH not on terminal carbon) alcohols. The number of carbon atoms in the alcohols of the present invention is typically (but not necessarily) less than 10, more typically less than 6, however longer-chain alcohols may be produced perhaps, in smaller amounts, and incorporated into the systems of the present invention.

The present invention describes methods and systems for the production of a bio-fuel. The process described herein comprises: converting biomass to alcohol(s) and residual biomass; gasifying the residual biomass to produce carbon monoxide, hydrogen, or mixtures thereof, thereby producing thermal energy; synthesizing a liquid hydrocarbon fuel from the alcohol(s) using some of the thermal energy produced by gasifying the residual biomass, integrating water from alcohol concentration to biomass pretreatment and hydrolysis, and integrating thermal energy from alcohol concentration and gasification to biomass pretreatment, hydrolysis, alcohol concentration, gasification, dehydration, and oligomerization. The individual steps or the building blocks have been previously shown to work independently, however the present invention provides a novel and unique way to combine the individual building blocks listed above to produce transportation fuels from a biomass.

Furthermore, the instant invention discloses specific integration embodiments leading to increased mass and energy efficiency. These include:

A. Residue Integration: The fermentation residue (e.g., lignin, unreacted cellulose and hemi-cellulose) is gasified and the syngas is fed to a cogeneration unit, which produces steam, heat, and electric power. The steam is used in the two reboilers and in the gasifier. The heat is used for dehydration and oligomerization.

B. Water Integration: The hot wastewater streams leaving the reboilers of the stripping and distillation columns are used for mass and heat integration by using them in pretreatment and hydrolysis thereby saving fresh water and heat needed in biomass pretreatment and hydrolysis C. Offgas Integration: The offgases from oligomerization are burned to provide steam needed in the process (e.g., pretreatment).

The methods and systems of the present invention enable the efficient production of liquid hydrocarbon fuels from biomass. Hydrocarbon fuels created by the present invention may include, but need not be limited to gasoline, diesel, kerosene, jet/aviation fuel, light heating oils, and drop-in substitutes for conventional transport fuels wherein these fuels meet the various standards set out by ASTM International and the U.S. E.P.A. In most cases, however, the fuels will not contain sulfur compounds and heavy metals at the levels found in conventional petroleum fuels.

The systems and methods of the present invention also allow for the production of organic chemicals such as olefins, paraffins, aromatics, and naphthenes. Of particular value are chemicals that may be used as feedstocks to the petrochemical industry such as ethylene, acetylene, benzene, cyclohexene, xylene, toluene, ethylbenzene, etc.

To counter depleting energy resources growing attention has been devoted to the conversion of biomass into fuel ethanol, considered as a fuel alternative or an additive to fossil fuels. Significant advances have been made towards the technology of ethanol fermentation including converting xylose to ethanol, utilization of cellulase enzyme in the hydrolysis of lignocellulosic materials, immobilization of microorganisms in large systems, simultaneous saccharification and fermentation (SSF) and sugar conversion into ethanol (Lin and Tanaka, 2006, relevant portions incorporated herein by reference).

The alcohol produced by the fermentation of the biomass can be catalytically converted to hydrocarbons, for e.g. Costa et al. (1985), relevant portions incorporated herein by reference, who studied the conversion of ethanol to hydrocarbons by use of a ZSM-5 zeolite catalyst. The effects of zeolite Si/Al ratio, ethanol dilution, and process variables (temperature, space velocity, pressure, and recycle rate of gaseous products) were also studied. In addition to catalytic conversion to hydrocarbons Whitcraft (1983) disclosed a method to directly recover gasoline from ethanol in fermentation broths. The method is a two-step process involving distilling a fermenter broth containing 8-10 wt % ethanol to a 90 wt % solution followed by dehydration wherein the concentrated ethanol solution is dehydrated to diethyl ether or fed directly to a conversion reactor where either the ether or ethanol is converted to gasoline by use of a suitable catalyst.

The alcohol produced by the fermentation as discussed above can be converted to gasoline-boiling-range hydrocarbons as described for the case of ethanol in, e.g., U.S. Pat. No. 4,621,164 (relevant portions incorporated herein by reference). The '164 patent involved contacting the ethanol in the vapor phase at dehydrating temperature with a bifunctional zeolite catalyst in the presence of an equimolar proportion of water. The catalyst induces simultaneous dehydration of the ethanol to reactive intermediates and recombination to a spectrum of hydrocarbons in the C1 to C10 range. Higher and lower proportions of water lead to higher yields of gaseous hydrocarbons.

Alternatively, the alcohols produced from the fermentation of the biomass are recovered and can be converted to other commercially valuable products and as starting materials for other reactions. Ethylene produced by the dehydration of ethanol in the presence of different catalysts (acid catalysts, metals, etc.) has been previously studied (Xiao et al., 2009, Ouyang et al., 2009, and Takahara et al., 2005, relevant portions incorporated herein by reference). The olefins (ethylene, propylene, butene, etc.) undergo further reactions to yield commercially important compounds.

For example, n-butenes can be dimerized to yield high octane gasoline components (Golombok and Bruijn, 2000, relevant portions incorporated herein by reference) or ethylene can be oligomerized catalytically in the presence of Ni-containing dealuminated Y-zeolites to yield linear and branched higher olefins, which are valuable feedstock, used in the manufacture of detergents, petrochemicals, oil additives, high-octane ecologic gasoline, etc. (Lallemand et al., 2006, relevant portions incorporated herein by reference).

The present invention may use a process for the production of a gasoline blending fraction rich in isooctane by the dimerization of isobutylene using tertiary butyl alcohol modifier and isoalkane diluent, such as that disclosed in U.S. Pat. No. 5,877,372 issued to Evans et al. (1999) relevant portions incorporated herein by reference; advantageously, the isobutylene is derived from the dehydration of tertiary butyl alcohol and the isoalkane used as diluent in the dimerization is the product formed by hydrogenation of the oligomerization product.

From the discussion hereinabove it is clear that biomass fermentation leading to the production of alcohol(s) is a starting point for a myriad of processes and reactions resulting in the production of commercially valuable products selected from the group consisting of hydrocarbons, gasoline, acids, ketones, ethers, alkylbenzenes, fuel additives, biopolymers, proteins for animal and human consumption, and surfactants. While these processes (or building blocks) generating these products have been individually studied and are functional, there is no common integrated unifying process design or method that combines all or elements of these individual building blocks. The present invention addresses this issue by describing a comprehensive integrated biofuel processing system to go from biomass to transportation fuel.

Biomass suitable for use with the systems and methods of the present invention may include, but need not be limited to, animal manures, kitchen waste, food processing waste, beverage waste, thin and whole stillage, wet distillers grain, raw human sewage, municipal solid waste, treated sewage sludges, fats, oils, greases, meat packing waste, paunche, tallows, processed lignocellulosic waste, pulp and paper sludges, wood wastes, landfill gas, digester gas, energy crops (cane, sorghum, miscanthus, switch grass or other), timber (poplar, aspen, willow, alder), crop residues (corn stover, wheat or rice straw, palm), algae, diatoms, seaweed, and other discarded vegetation including municipal grass and timber wastes. Municipal solid waste may include items that are not of (recent) biological origin but, nonetheless, may be processed by the systems of the invention. Such non-biological materials may include, but need not be limited to, plastics, solvents, used motor oil, and construction debris.

Residual biomass typically comprises the solid materials that remain after biomass has undergone a biomass conversion process described herein. In some cases the biomass is "fractionated" before undergoing the conversion process described herein. "Fractionation" involves decomposing the biomass into its constituent parts of cellulose, hemi-cellulose, and lignin. If biomass fractionation is purposely used before fermentation to separate cellulose, hemicelluloses, and lignin, then the residual biomass may include a specific cut such as lignin. Residual biomass typically has lower cellulose content in comparison to virgin biomass because the biomass conversion process preferentially results in the degradation of cellulose.

Briefly, a biomass prior to the conversion process described herein is subjected to a pretreatment and a hydrolysis step. The pretreatment step liberates cellulose and hemicellulose from the lignin and involves, e.g., the use of thermal, physical, and chemical methods such as hot-water pretreatment, steam explosion, ozonolysis, ammonia fiber expansion, weak- and strong-acid hydrolysis, alkaline wet oxidation and supercritical $CO_2$ extraction. The hydrolysis step breaks down the cellulosic and hemicellulosic chains to simple sugars (e.g., glucose, xylose, etc.). The process can also treat the hemicellulose to produce C5 sugars that are different from those obtained from cellulose and these require different subsequent treatments for conversion to alcohols. Hydrolysis may be carried out via chemical methods (e.g., the use of dilute or concentrated acids) or enzymatic methods. Conversion into alcohols (preferably but not necessarily ethanol) (e.g., using anaerobic fermentation), concentration of the alcohol using stripping and distillation, membrane separation, or molecular sieves. Dehydration of the alcohol into the corresponding olefin (ethanol could be converted into ethylene) can be accomplished by, e.g., vapor phase reaction over a solid acid catalyst, and oligomerization of the ethylene into transportation fuels (e.g., using ZSM-5 or other catalysts possibly containing metals or non-metals in their matrices).

The different processes in the integrated biofuel processing system of the present invention is described herein below and is also depicted schematically in FIG. 1. The system comprises the following main subsystems or processes:

The Biomass Conversion System: This includes:

Pretreatment: Breaks down the cellulose and hemicellulose materials in the biomass by a cavitation method, micronization methods, chemical treatment methods, grinding methods or any other suitable method.

Hydrolysis: The hydrolysis step converts the pretreated cellulose and hemicellulose materials into sugars.

Fermentation: In this step the mixture of water and processed feedstocks are typically allowed to ferment at elevated temperatures to produce alcohols. The fermentation proceeds until the alcohol content reaches approximately 16%. At the end of this step the resultant mixture of water, feedstock and alcohol is then separated, with the residual biomass being fed to the gasification subsystem Stripping and Distillation: In this step the water and alcohol mixture without the biomass is passed through a stripping column and the distillation column to produce a clean stream of alcohol that can be fed to the a dehydration subsystem and/or the fuel conversion subsystem.

Dehydration and Fuel Conversion System: This includes:

Dehydration: In this step the alcohol received from the biomass conversion system is converted to form an alkene (olefin) and includes a water separator. When ethanol is received it is converted to ethylene or other chemicals.

Oligomerization: The fuel conversion system produces a mixture of liquid hydrocarbons (e.g. gasoline) from the alcohols. The fuel conversion system utilizes an oligomerization process to perform the conversion of olefins (such as ethylene) to fuel.

Gasification System: This includes:

Gasification: In this step the residual biomass from the fermenter is converted to heat and product gases by thermal conversion at high temperatures. Gasification typically involves the conversion of residual biomass to a mixture of carbon monoxide and hydrogen, generally known as "syngas."

Cogeneration: The syngas produced from gasification is fed to a cogeneration unit which produces steam, energy as heat (from the hot off-gasses) and electric power. The steam from the cogeneration system can be used by the gasifier and by reboiler systems. The heat from the hot-gasses of the cogeneration system can be used by the dehydration and fuel generation subsystems. The hot water produced from the reboilers can be used by the stripping and distillation columns and can also be used for mass and heat integration in the pretreatment system and the hydrolysis system, thereby saving fresh water and heat needed in the pretreatment and hydrolysis systems.

Thus, from the above description it can be seen that some of the interconnections represent the transport of materials, such as the transfer of residual biomass from the biomass conversion subsystem to the gasification subsystem. Some of the other interconnections the transfer of thermal energy between the interdependent subsystems. Such transfer may include, but need not be limited to, the recovery of "waste heat" from the gasification subsystem to meet the heating needs of the biomass conversion system. Thermal energy may be recovered from a number of other process steps present in the biomass conversion, gasification, or fuel conversion subsystems.

An overview of the system and methods of the present invention are shown in FIG. 1. Integrated biofuel production systems of the invention 10 may be visualized as at least four interdependent subsystems symbiotically sharing by-product or waste materials and/or thermal energy that have traditionally been discarded. The four subsystems are a biomass conversion subsystem 12, a gasification subsystem 14, a dehydration subsystem 16, and a fuel conversation subsystem 18. While the production system may be conceptualized as four interdependent subsystems (12-18), a given embodiment of the invention may not have readily recognizable subsystems because of the need to interconnect sinks and sources of materials and thermal energy in order to maximize efficiency. However, the interconnections allow the integrated biofuel production systems 10 of the present invention to use materials and thermal energy most efficiently, thus making it possible to produce more liquid fuel from less biomass, while using less external energy to drive the process.

The biomass conversion subsystem 12 of the present invention may entail any of a number of known methods suitable for converting biomass into an alcohol and residual biomass. Such methods may include, but need not be limited to, the fermentation of biomass to alcohols 20, and enzymatic conversion of sugars to alcohols or acids. The acids can then be further converted to alcohols. The methods of the present invention need not be limited to a singular biomass conversion system 12, as it may be beneficial to incorporate more than one type of biomass conversion system 12 into a given biofuel processing system.

In one embodiment the biomass conversion subsystem 12 consists of a pretreatment subsystem, a hydrolysis subsystem 24 and a fermentation subsystem 20. The pretreatment process may be any known process that works to break down cellulose and hemicellulose materials, such as cavitation methods, micronization methods, chemical treatment methods, grinding methods or any other suitable method. For example, biomass grains can be crushed, ground or enzymatically treated to make the sugars in the feedstock more accessible for the microorganism (e.g., yeast) that will ferment the sugars to alcohol. An additional hydrolysis subsystem 26 may be used to acid hydrolyze cellulosic materials to produce free sugars.

The pretreated and hydrolyzed biomass and sugars are fed into the fermentation subsystem 20. In the fermentation subsystem 20, a mixture of water and processed feedstocks are typically allowed to ferment at elevated temperatures until the alcohol content reaches approximately 16%. The resultant mixture of water, feedstock and alcohol is then separated, with the residual biomass being fed to the gasification subsystem 28, and the water and alcohol mixture passing through a stripping column 30 and the distillation column 32 to produce a clean stream of alcohol that can be fed to the a dehydration subsystem 16 and/or the fuel conversion subsystem 18. Other separation methods (e.g., membranes) may be used to concentrate the alcohols. The alcohols need not be concentrated to high levels of purity. For instance, in the case of ethanol, there is no need to exceed the azeotropic concentration. Suitably, the ethanol concentration on the resulting ethanol/water mixture after stripping and distillation may be 94% ethanol or less. Suitably, the distillation column 32 has a partial condenser that allows the top product to leave the distillation column as azeotropic ethanol vapor.

The gasification subsystem 18 of the present invention may entail any number of known methods suitable for converting residual biomass to heat and product gases by thermally converting the residual biomass at high temperatures. Gasification typically involves the conversion of residual biomass to a mixture of carbon monoxide and hydrogen, generally known as "syngas." In the gasification process 20, residual biomass from the biomass conversion subsystem is collected and dried to achieve approximately 10% moisture content. The dried biomass is then preheated using a steam driven heat exchanger. The hot, dried, residual biomass is then injected into a gasification reactor where the residual biomass is burned in the presence of air and/or steam at approximately a temperature of 800-1400° C., preferably at a temperature of 950-1150° C. Because of the higher temperatures and the presence of oxygen, the residual biomass is converted almost entirely to a clean syngas, leaving only a small amount of char that can be sold as a byproduct. The addition of steam enhances the hydrogen yield in the produced syngas. The resultant syngas can be cooled by a heat exchanger, the thermal energy captured in the heat exchanger being circulated to another subsystem of the biofuel processing system, where the thermal energy can be used to preheat other processes. Gasification reactors suitable to be used as subsystems for the present invention may be obtained commercially.

The syngas produced from gasification is used in a cogeneration unit 34 which produces steam, energy as heat (from the hot off-gasses) and electric power. The steam from the cogeneration system can be used by the gasifier and by reboiler systems. The heat from the hot-gasses of the cogeneration system 34 can be used by the dehydration 20 and fuel generation subsystems 18. The hot water produced from the reboilers can be used by the stripping 30 and distillation columns 32 and can also be used for mass and heat integration in the pretreatment system 24 and the hydrolysis system 26, thereby saving fresh water and heat needed in the pretreatment 24 and hydrolysis systems 26.

The interconnections between subsystems of the biofuel processing system 10 are also shown in FIG. 1. Some of the interconnections represent the transport of materials, such as the transfer of residual biomass from the biomass conversion subsystem 12 to the gasification subsystem 18. Some of the other interconnections the transfer of thermal energy between the interdependent subsystems. Such transfer may include, but need not be limited to, the recovery of "waste heat" from the gasification subsystem 14 to meet the heating needs of the biomass conversion system 12. Thermal energy may be recovered from a number of other process steps present in the biomass conversion 12, gasification 14, or fuel conversion sub systems 18.

One of skill in the art appreciates that capturing and transporting thermal energy as well as residual biomass and gasses requires transfer systems that are not shown in FIG. 1. For example, a number of conveyors and pumps will be needed to move materials and thermal loads between subsystems. Heat transfer systems may rely on pressurized water or other known heat-transfer fluids to recover the heat and to serve as a heat-transfer medium between the various components of the subsystems. Heat transfer systems may also include exchanging heat directly between process hot streams and process cold streams. Heat transfer systems appropriate for use in the invention are known to those of skill in the art, and are commercially available. In some embodiments, it may be beneficial to produce steam from excess thermal energy, which may be used for both heating processes and to provide electrical energy (by driving a turbine) to power the transfer systems.

While it is possible to produce electricity to drive the heat and material transfer processes with steam, in many cases it is more efficient to use the thermal energy produced by the subsystems for heating rather than electrical production. Optimally, if additional heat and power are needed, the heat and material transfer systems can be powered from other renewable energy sources amenable to the production of electricity, such as wind turbines, solar panels, or a biogas-powered electrical generator. However, the transfer systems can also be powered with electricity from the local power grid.

A dehydration subsystem 36 may be used to convert the alcohol received from the biomass conversion system to form an alkene (olefin) and includes a water separator 38. When ethanol is received it is converted to ethylene or other chemicals.

The fuel conversion subsystem 18 can be adapted to create liquid hydrocarbon fuel, such as gasoline, jet fuel, and/or diesel from the alcohol or olefin received from the dehydration subsystem. Olefins may be directly oligomerized to hydrocarbons in high temperatures (300-450° C.) and moderate pressures (1-40 atm) in the presence of a catalyst in an oligomerization reactor 40. Suitably the catalyst is a zeolite catalyst or other solid acid catalyst, possibly with added metals or rare earths. By controlling the temperature and pressure of the oligomerization process and/or the composition of the catalyst, it is possible to direct the production of longer or shorter chain hydrocarbons. It is also possible to control the amount of alkane branching in the final product. The thermal energy required for the oligomerization process may be augmented with thermal energy taken from the gasification sub system 14.

In some embodiments, oligomerization reactor 40 may produce an amount of residual light hydrocarbons (light-ends), e.g. short chain liquid and gaseous hydrocarbons including those for combustion 42. These light ends may be thermally reformed with steam to produce methanol and other primary alcohols, which can be fed into the oligomerization reactor in order to boost the fuel output. In other embodiments, the light ends may be recycled to create methanol and the methanol converted to long chain liquid hydrocarbons using the MOBIL methanol to fuel process.

The gasification system described above is intended to be illustrative, and is not intended to limit the scope of the invention. Other methods of producing energy as heat and process gasses from residual biomass are also known to those of skill in the art. For example, the residual biomass may be dried and pelletized for use directly in burners and or boilers to provide heat for various processes requiring the additional of thermal energy. Additionally, it is anticipated that new methods for producing heat and process gasses are likely to be discovered in the near future.

The biomass conversion systems 10 detailed above are intended to be illustrative, and are not intended to limit the scope of the invention. Other methods of producing useful feedstocks for the fuel conversion subsystem are also known to those of skill in the art. Additionally, it is anticipated that new methods for converting biomass to methane or alcohol and residual biomass are likely to be discovered in the near future.

In conclusion, the present invention permits, for the first time, the integration of existing/known technologies in a unique, non-obvious way to create an overall pathway from biomass to bio-fuels that others have not recognized. The present inventors have found that the present invention allows for the shortest or minimum path between biomass and fuels, that is, the simplest, most direct and shortest path from biomass to transportation fuels with alcohols as intermediates, while avoiding the use of hydrogen during the processing steps. Furthermore, the present invention allows the user to "drop-in" substitutable fuels because the products produced hereby (bio-gasoline, bio jet and bio-diesel) are direct substitutes for conventional petroleum based fuels. They can be used as-is without modifications to engines or distribution infrastructure. Additionally, the integration of mass and energy in novel ways throughout the process enhance the overall efficiency of the process. The efficiency of the conversion process is enhanced by utilizing heat and mass from one process as an ingredient to another process. Thus, the biomass processing system may enable a relatively high degree of yield and an enhanced usage of fresh water and thermal energy in relation to the amount of biomass introduced into the biofuel processing system.

Although the present invention has been described with several embodiments, a myriad of changes, variations, alterations, transformations, and modifications may be suggested to one skilled in the art, and it is intended that the present disclosure encompass such changes, variations, alterations, transformation, and modifications as they fall within the scope of the appended claims.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 6,620,292: Cellulose production from lignocellulosic biomass.
United States Patent Application No. 20050269048: Novel catalytic reactor process for the production of commercial grade pulp, native lignin & unicellular protein.
U.S. Pat. No. 4,621,164: Hydrocarbon production.
U.S. Pat. No. 5,877,372: Isobutylene oligomerization using isooctane diluent.
Costa, E., Ugulna, A., Aguado, J. and Herndndez, P. J. Ethanol to Gasoline Process: Effect of Variables, Mechanism, and Kinetics. *Ind. Eng. Chem. Process Des. Dev.* (1985) 24: 239-244.
Golombok, M. and de Bruijn, J. Dimerization of n-Butenes for High Octane Gasoline Components. *Ind. Eng. Chem. Res.* (2000) 39, 267-271.
Lallemand, M., Finiels, A., Fajula, F. and Hulea, V. Catalytic oligomerization of ethylene over Ni-containing dealuminated Y zeolites. Applied Catalysis A: General (2006) 301 196-201.
Lin, Y. and Tanaka, S. Ethanol fermentation from biomass resources: current state and Prospects. *Appl. Microbiol. Biotechnol.* (2006) 69: 627-642.
Ouyang, J., Kong, F., Su, G., Hu, Y. and Song, Q. Catalytic Conversion of Bio-ethanol to Ethylene over La-Modified HZSM-5 Catalysts in a Bioreactor. *Catalysis Letters* (2009) 132 (1-2), 164-174.
Takahara, I., Saito, M., Inaba, M. and Murata, K. Dehydration of ethanol into ethylene over solid acid catalysts. *Catalysis Letters* (2005) 105 (3-4) 249-252.
Xiao, Y., Li, X., Yuan, Z., Li, J. and Chen, Y. Catalytic Dehydration of Ethanol to Ethylene on $TiO_2/4A$ Zeolite Composite Catalysts. *Catal. Lett.* (2009) 130:308-311.
Whitcraft, D. R., Veryklos, X. E. and Yutharasan, R. Recovery of Ethanol from Fermentation Broths by Catalytic Conversion to Gasoline. *Ind. Eng. Chem. Process Des. Dev.* (1983) 22: 452-457.

What is claimed is:

1. An integrated biofuel production process comprising the steps of:
   (a) converting a biomass to yield one or more alcohols and a residual biomass;
   (b) gasifying the residual biomass to produce carbon monoxide, hydrogen or mixtures thereof, thereby producing thermal energy;
   (c) synthesizing a liquid hydrocarbon fuel from the alcohols through a dehydration and an oligomerization reaction using at least a portion of the thermal energy produced by gasifying the residual biomass;
   (d) converting the residual biomass into energy and/or one or more commercially viable co-products, wherein the co-products are selected from the group consisting of acids, ketones, alcohols, ethers, alkylbenzenes, fuel additives, biopolymers, proteins for animal and human consumption, and surfactants; and (e) further comprising the step of combusting the carbon monoxide, the hydrogen, or mixtures thereof to produce heat and electricity, wherein the heat and electricity are recycled back into the process to perform step (c).

2. The process of claim 1, wherein at least a portion of the thermal energy produced by the gasification of the residual biomass is recycled back into the process to perform step (a).

3. The process of claim 1, wherein step (a) includes a pretreatment process and a hydrolysis process, wherein the pretreatment and hydrolysis processes are done by using a hot wastewater.

4. The process of claim 1, wherein the biomass is selected from the group consisting of grasses, trees, canes, animal waste, food waste, algae, municipal solid waste green waste, purpose grown non-food energy crops, harvest residuals, and other waste and crop biomass materials.

5. The process of claim 1, wherein the one or more alcohols generated in step (a) are further converted to one or more olefins by a dehydration reaction, wherein the one or more olefins are selected from the group consisting of ethylene, propylene, butene, iso-butylene, and combinations and modifications thereof.

6. The process of claim 5, wherein the one or more olefins undergo an oligomerization in an oligomerization reactor in step (c) to generate one or more commercially viable products selected from the group consisting of chemicals, transportation fuels, linear and branched higher olefins, feedstock, detergents, petrochemicals, oil additives, and high-octane gasoline.

7. The process of claim 1, wherein the alcohol is ethanol, wherein the ethanol is further dehydrated in the process to yield ethylene.

8. The process of claim 1, wherein step (c) further comprises an oligomerization step for converting the olefin (e.g., ethylene) to a hydrocarbon fuel.

9. A chemical production process comprising the steps of:
(a) converting a biomass to one or more alcohols and a residual biomass;
(b) gasifying the residual biomass to produce one or more hydrocarbon gasses, carbon monoxide, hydrogen or mixtures thereof;
(c) synthesizing one or more chemicals from the alcohols and the hydrocarbon gases, carbon monoxide, hydrogen, or mixtures thereof; and
(d) combusting the hydrocarbon gasses, the carbon monoxide, the hydrogen, or mixtures thereof to produce heat and electricity, wherein the heat and electricity are recycled back into the process to perform step (c).

10. The process of claim 9, wherein the chemicals is selected from the group consisting of paraffins, olefins, aromatics, and naphthas.

11. The process of claim 9, wherein the chemical is selected from the group consisting of ethylene, acetylene, benzene, cyclohexene, xylene, toluene, ethylbenzene.

12. A process for making one or more hydrocarbon fuels from one or more alcohols comprising the steps of:
(a) dehydrating the one or more alcohols to yield one or more olefins; and
(b) oligomerizing the one or more olefins in an oligomerization reactor to yield one or more commercially viable products selected from the group consisting of chemicals, transportation fuels, linear and branched higher olefins, feedstock, detergents, petrochemicals, oil additives, and high-octane gasoline; and
(c) combusting a carbon monoxide, a hydrogen, or mixtures thereof from a biomass to produce heat and electricity, wherein the heat and electricity are recycled back into the process to perform step (c).

13. The process of claim 12, wherein the process is a "stand-alone" process or can be implemented as a "bolt-on" addition to existing alcohol producing plants.

14. An integrated biofuel production process comprising the steps of:
(a) pretreating a biomass;
(b) hydrolyzing the converted biomass, wherein the pretreatment and hydrolysis processes are done by using a hot wastewater;
(c) converting a biomass to yield one or more alcohols and a residual biomass;
(d) gasifying the residual biomass to produce carbon monoxide, hydrogen or mixtures thereof, thereby producing thermal energy, wherein at least a portion of the thermal energy produced by the gasification of the residual biomass is recycled back into the process to perform step (c);
(e) synthesizing a liquid hydrocarbon fuel from the alcohols using at least a portion of the thermal energy produced by gasifying the residual biomass;
(f) converting the residual biomass into one or more commercially viable co-products, wherein the co-products are selected from the group consisting of acids, ketones, alcohols, ethers, alkylbenzenes, fuel additives, biopolymers, proteins for animal and human consumption, and surfactants; and
(g) further comprising the step of combusting the carbon monoxide, the hydrogen, or mixtures thereof to produce heat and electricity, wherein the heat and electricity are recycled back into the process to perform step (c).

15. The process of claim 14, wherein the biomass is selected from the group consisting of grasses, trees, canes, animal waste, food waste, algae, municipal solid waste green waste, purpose grown non-food energy crops, harvest residuals, and other waste and crop biomass materials.

16. The process of claim 14, wherein the one or more alcohols generated in step (a) are further converted to one or more olefins by a dehydration reaction, wherein the one or more olefins are selected from the group consisting of ethylene, propylene, butene, iso-butylene, and combinations and modifications thereof.

* * * * *